United States Patent
She et al.

(10) Patent No.: US 12,032,031 B2
(45) Date of Patent: Jul. 9, 2024

(54) ADAPTIVE CONTROL METHOD FOR MOBILE X-RAY MACHINE, AND HIGH VOLTAGE GENERATOR

(71) Applicant: Delta Electronics (Shanghai) Co., Ltd., Shanghai (CN)

(72) Inventors: Chang She, Shanghai (CN); Hongyuan Jin, Shanghai (CN); Yao Tao, Shanghai (CN); Tianwei Wang, Shanghai (CN); Liangyuan Pu, Shanghai (CN); Xintian Li, Shanghai (CN)

(73) Assignee: DELTA ELECTRONICS (SHANGHAI) CO., LTD., Shanghai (CN)

( * ) Notice: Subject to any disclaimer, the term of this patent is extended or adjusted under 35 U.S.C. 154(b) by 526 days.

(21) Appl. No.: 17/231,161

(22) Filed: Apr. 15, 2021

(65) Prior Publication Data

US 2021/0325474 A1    Oct. 21, 2021

(30) Foreign Application Priority Data

Apr. 20, 2020    (CN) .......................... 202010309909.0

(51) Int. Cl.
| | |
|---|---|
| G01R 31/3842 | (2019.01) |
| A61B 6/00 | (2006.01) |
| G01R 31/396 | (2019.01) |
| H05G 1/10 | (2006.01) |

(52) U.S. Cl.
CPC ............ *G01R 31/3842* (2019.01); *A61B 6/56* (2013.01); *G01R 31/396* (2019.01); *H05G 1/10* (2013.01)

(58) Field of Classification Search
CPC ............. G01R 31/3842; G01R 31/396; G01R 31/382; A61B 6/56; A61B 6/4405; A61B 6/00; H05G 1/10; H02J 7/345
See application file for complete search history.

(56) References Cited

U.S. PATENT DOCUMENTS

| | | | | |
|---|---|---|---|---|
| 2015/0008867 | A1* | 1/2015 | Smychkovich | ........... H02J 7/00 320/137 |
| 2017/0020480 | A1* | 1/2017 | Hishikawa | ............. A61B 6/467 |
| 2018/0354633 | A1* | 12/2018 | Wang | ........................ H02J 7/32 |

FOREIGN PATENT DOCUMENTS

| | | |
|---|---|---|
| CN | 101026316 A | 8/2007 |
| CN | 105610302 A | 5/2016 |
| CN | 105406542 B | 9/2018 |

\* cited by examiner

*Primary Examiner* — David P Porta
*Assistant Examiner* — Mamadou Faye
(74) *Attorney, Agent, or Firm* — NIXON PEABODY LLP

(57) ABSTRACT

An adaptive control method for a mobile X-ray machine includes: acquiring operating information of a battery, determining a state of the battery; if the battery is in a failure state, selecting a first control value; if the battery is not in the failure state, determining whether a residual charge of the battery is less than a low charge threshold; if the residual charge of battery is less than low charge threshold, determining the battery is in a low charge state, and selecting a second control value; and if residual charge of battery is not less than low charge threshold, determining the battery is in a normal state, and selecting a third control value; acquiring circuit parameter information of a capacitor charger, and controlling capacitor charger based on circuit parameter information and the first control value or the second control value or the third control value.

15 Claims, 5 Drawing Sheets

ADAPTIVE CONTROL METHOD FOR MOBILE X-RAY MACHINE, AND HIGH VOLTAGE GENERATOR

CROSS REFERENCES TO RELATED APPLICATION

The present application claims priority to Chinese patent application No. 2020103099090, filed on Apr. 20, 2020, the content of which is hereby incorporated by reference in its entirety.

TECHNICAL FIELD

The present disclosure relates to the field of an X-ray machine, and particularly to an adaptive control method for a mobile X-ray machine and a high voltage generator.

BACKGROUND

The mobile X-ray machine can diagnose outdoors, and obtain X-ray images of patients or animals conveniently and quickly to diagnose the patients or animals. So the mobile X-ray machine plays an extremely important role in outdoor diagnosis, emergency rescue and disaster relief, and the like.

The mobile X-ray machine generally needs to be equipped with a large-capacity battery, and X-ray generating unit can be powered by the large-capacity battery and a grid together. However, when the battery is in the failure state, the mobile X-ray machine cannot work under the condition that the X-ray generating unit is only powered by the grid. The existing high voltage generator cannot achieve an adaptive control according to different working states of the battery (such as normal battery, battery failure, battery under voltage, and other states), and accordingly has a disadvantage of low reliability.

SUMMARY

In a first aspect, the present disclosure provides an adaptive control method for an X-ray machine, which includes: acquiring operating information of a battery, and determining a state of the battery; if it is determined that the battery is in a failure state, selecting a first control value; if it is determined that the battery is not in the failure state, determining whether a residual charge of the battery is less than a low charge threshold; if the residual charge of the battery is less than the low charge threshold, determining that the battery is in a low charge state, and selecting a second control value; if the residual charge of the battery is not less than the low charge threshold, determining that the battery is in a normal state, and selecting a third control value; and acquiring circuit parameter information of a capacitor charger, and controlling the capacitor charger based on the circuit parameter information and the first control value or the second control value or the third control value.

In a second aspect, the present disclosure provides an adaptive control method for an X-ray machine, which includes: acquiring operating information of a battery, and determining whether the battery is in a failure state; if the battery is in the failure state, selecting a first control value; if it is determined that the battery is not in the failure state, selecting a third control value; acquiring circuit parameter information of a capacitor charger, and controlling the capacitor charger based on the circuit parameter information and the first control value or the third control value.

In a third aspect, the present disclosure provides a high voltage generator, which includes: a battery charger, an input end of the battery charger being configured to electrically connect to a grid; a battery, connected to an output end of the battery charger electrically; a capacitor charger, an input end of the capacitor charger being electrically connected to the battery; an energy storage capacitor, connected to an output end of the capacitor charger electrically; a high voltage conversion circuit, electrically connected between the energy storage capacitor and an X-ray generating unit, to power the X-ray generating unit; and a control unit, electrically connected to the battery and the capacitor charger, and configured to acquire operating information of a battery, and determine a state of the battery; wherein, the control unit selects a first control value if the battery is in a failure state; and if the battery is not in the failure state, the control unit determines whether a residual charge of the battery is less than a low charge threshold; if the residual charge of the battery is less than the low charge threshold, the control unit determines that the battery is in a low charge state, and selects a second control value; if the residual charge of the battery is not less than the low charge threshold, the control unit determines that the battery is in a normal state, and selects a third control value; and the control unit acquires circuit parameter information of a capacitor charger, and controls the capacitor charger based on the circuit parameter information and the first control value or the second control value or the third control value.

BRIEF DESCRIPTION OF THE DRAWINGS

In order to more clearly illustrate the technical solutions of the embodiments of the present disclosure or of the conventional technology, the accompanying drawings used in the description of the embodiments or the conventional technology are briefly described below. Apparently, the accompanying drawings in the following description are merely some embodiments of the present disclosure, and those of ordinary skill in the art can obtain other drawings according to these accompanying drawings without creative work.

DETAILED DESCRIPTION

In order to make the above objectives, features and advantages of the present disclosure more apparent and easier to understand, embodiments of the present disclosure will be detailed hereinafter with reference to the accompanying drawings. Numerous specific details are set forth in the following description in order to fully understand the present disclosure. However, the present disclosure can be implemented in many other modes different from those described herein, and a person skilled in the art can make similar improvements without departing from the spirit of the present disclosure, and thus, the present disclosure is not limited by the specific embodiments disclosed below.

It should be understood that when an element is referred to as "fixed to" another element, the element may be directly provided on the other element or there is an intermediate element. When an element is considered to be "connected" to another element, the element may be directly connected to the other element or there is an intermediate element at the same time.

All technical and scientific terms used herein have the same meaning as commonly understood by one of ordinary skill in the art to which this disclosure applies, unless otherwise defined. The terms used in the specification of present disclosure are only for the purpose of describing specific embodiments and are not intended to limit the present disclosure. The term "and/or" used herein includes any and all combinations of one or more associated listed items.

Figure 1:
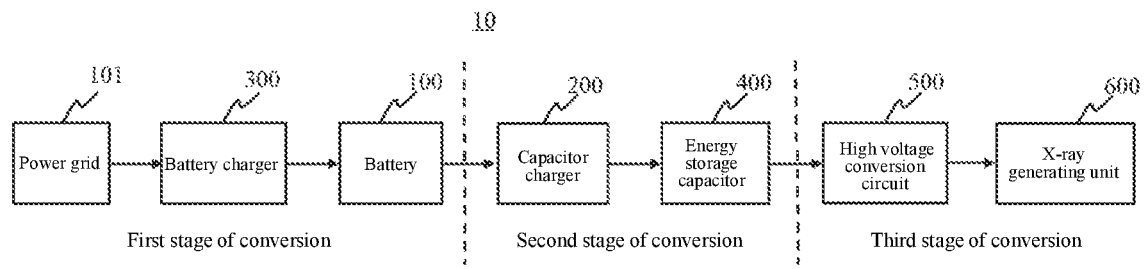
FIG. 1 is a schematic block diagram of a high voltage generator according to an embodiment of the present disclosure.

Referring to FIG. 1, which is a schematic structure diagram illustrating a high voltage generator 10 applied to an X-ray machine. As shown in FIG. 1, the high voltage generator 10 may include three stages of conversion. In a first stage of conversion, a battery 100 and a battery charger 300 are included. An input end of the battery charger 300 is configured to electrically connect to a power grid 101. An output end of the battery charger 300 is electrically connected to the battery 100. The battery charger 300 receives a grid voltage to charge the battery 100. In a second stage of conversion, a capacitor charger 200 and an energy storage capacitor 400 are included. An input end of the capacitor charger 200 is electrically connected to the battery 100. An output end of the capacitor charger 200 is electrically connected to the energy storage capacitor 400. In a third stage of conversion, a high voltage conversion circuit 500 and an X-ray generating unit 600 are included. An input end of the high voltage conversion circuit 500 is electrically connected to the energy storage capacitor 400. An output end of the high voltage conversion circuit 500 is connected to the X-ray generating unit 600. The present disclosure mainly aims to achieve an adaptive control of the capacitor charger 200 in the second stage of conversion for different working conditions of the battery in the first stage of conversion, such as normal battery, battery failure, battery under voltage, and the like.

Figure 2:
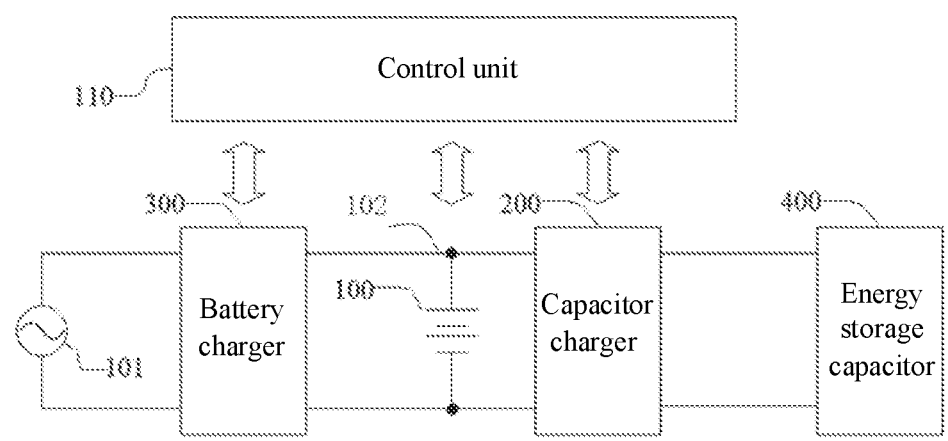
FIG. 2 is a partial schematic block diagram of a high voltage generator according to an embodiment of the present disclosure.

In an embodiment, as shown in FIG. 2, the high voltage generator 10 further includes a control unit 110. The form of the control unit 110 is not limited in the present disclosure. In some embodiments, the control unit 110 may include a plurality of control panels, and different control panels perform different functions. In some embodiments, the control unit 110 may include a digital processing chip such as a single chip microcomputer or a digital signal processor (DSP). The control unit 110 can implement the acquisition and operation of information of the battery 100, the capacitor charger 200, and the like, and can implement control of the battery charger 300 and the capacitor charger 200, and the like, which are all within the protection scope of the present disclosure. In some embodiments, the control unit may further include a plurality of controllers, and different controllers perform different functions and operations, which is not limited by the present disclosure.

Figure 3:
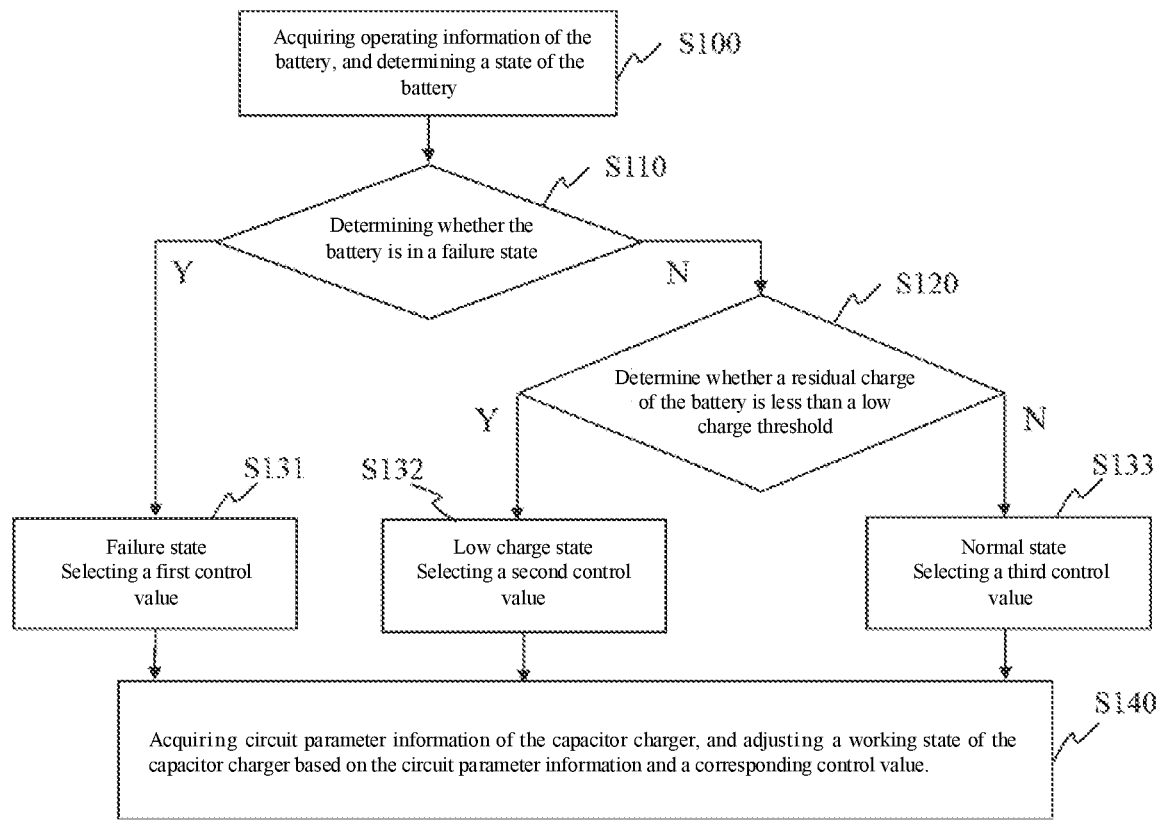
FIG. 3 is a flow chart of an adaptive control method according to an embodiment of the present disclosure.

Further, an embodiment of the present disclosure provides an adaptive control method. As shown in FIG. 3, the adaptive control method specifically includes following steps.

S100: acquiring operating information of the battery 100, and determining a state of the battery.

In an embodiment, the operating information of the battery 100 can be acquired and the state of the battery can be determined by the control unit 110. For example, the battery 100 may be in a failure state, a low charge state, or a normal state. Specifically, in some embodiments, the control unit 110 may acquire the operating information of the battery 100 through a battery management system. The battery management system can monitor the operating information of the battery 100 in real time, and record the operating information of the battery 100 in real time, so as to facilitate a subsequent query and retrieval. The operating information of the battery may include: fault information, battery voltage, battery current, state of charge (SOC) information, and the like. The control unit 110 can acquire the operating information of the battery 100 stored in the battery management system through a communication mode. In some embodiments, the control unit can further detect a bus voltage of the battery through a sampling circuit, and obtain charge information and fault information of the battery through calculation and determination. The present disclosure is not limited thereto.

S110: Determining whether the battery is in a failure state. If the battery 100 is in the failure state, step S131 is performed.

S131: Selecting a first control value.

In some embodiments, if it is determined that the battery 100 is in a failure state, then the control unit 110 selects the first control value $C_1$. Specifically, the control unit 110 loads the first control value $C_1$ to control the capacitor charger 200. In an embodiment, the first control value $C_1$ may be a voltage control signal or a current control signal or a power control signal. Further, if the battery 100 does not fail, that is, the battery 100 is not in a failure state, step S120 is performed.

S120: Determining whether a residual charge of the battery is less than a low charge threshold.

If the residual charge of the battery 100 is less than the low charge threshold, S132 is performed.

S132: Selecting a second control value.

If the residual charge of the battery 100 is not less than the low charge threshold, S133 is performed.

S133: Selecting a third control value.

In an embodiment, if the control unit 110 determines that the battery 100 does not fail, the control unit 110 further determines whether the residual charge of the battery 100 is too low according to the state information. Specifically, the control unit 110 can compare the residual charge of the battery 100 to the low charge threshold. If the residual charge of the battery 100 is less than the low charge threshold, it is determined that the residual charge of the battery 100 is too low and the battery is in a low charge state.

At this time, the control unit 110 can load the second control value $C_2$ to control the capacitor charger 200. If the residual charge of the battery 100 is greater than or equal to the low charge threshold, it indicates that the residual charge of the battery 100 is normal, that is, the battery is in a normal state. At this time, the control unit 110 can load a third control value $C_3$ to control the capacitor charger 200.

In an embodiment, the low charge threshold can be set according to actual acquirements. For example, the low charge threshold may be 10% or 8% of a rated capacity of the battery 100, or the like, and the present disclosure is not limited thereto. In some embodiments, the first control value $C_1$, the second control value $C_2$, and the third control value $C_3$ may be voltage control signals, current control signals, or power control signals. In some embodiments, the first control value $C_1$ can be equal to the second control value $C_2$. In other embodiments, the second control value $C_2$ can be equal to the third control value $C_3$, and the present disclosure is not limited thereto.

S140: Acquiring circuit parameter information of the capacitor charger, and controlling the capacitor charger based on the circuit parameter information and a corresponding control value.

In an embodiment, the control unit 110 acquires the circuit parameter information of the capacitor charger 200, and controlling the capacitor charger 200 based on the circuit parameter information and the first control value or the second control value or the third control value. In an embodiment, the circuit parameter information may include at least one of an output power, an input power, an input voltage, an input current, or an output current of the capacitor charger 200.

Wherein, the sequence of the S110 and S120 can be changed. Through the determinations of the steps S110 and S120, the state of the battery can be summarized as three types: failure state, low charge state, normal state. When the battery is in the failure state, the battery is disconnected from the circuit, and the battery cannot be charged or discharged, so the control unit 110 loads the first control value. When the battery is in the low charge state, although the battery does not fail, the battery can only be charged or discharged with low charge or low power. So the battery in the second type state needs to be charged as soon as possible, and the control unit 110 loads the second control value. The third type state is a normal state. The battery operates normally and can be charged or discharged within a battery specification range, and the control unit 110 loads the third control value.

Figure 4:
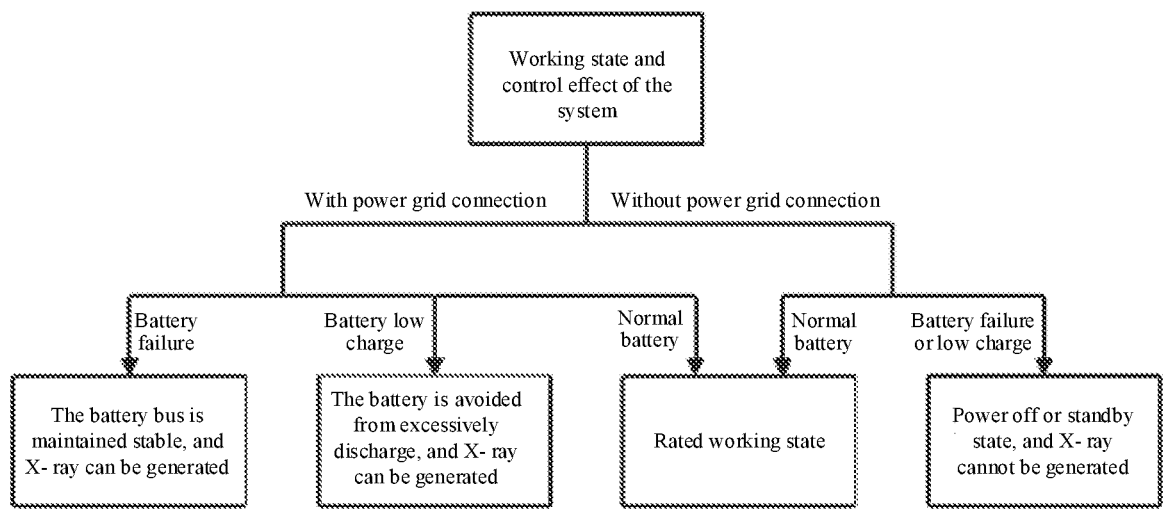
FIG. 4 is a schematic diagram showing working state of the mobile X-ray machine according to an embodiment of the present disclosure.

In some embodiments, the above determination is based on the case where the battery charger 300 is connected to the power grid 101. In practice, the battery charger 300 may not be connected to the power grid 101. FIG. 4 is a schematic diagram showing working states of the mobile X-ray machine according to an embodiment of the present disclosure. As shown in FIG. 4, there are two situations for consideration according to whether the battery charger 300 is connected to the power grid.

If the input end of the battery charger 300 is connected to the power grid 101, when the battery 100 is in a failure state, the battery 100 may not work normally. However, since the battery charger 300 in the first stage of conversion can provide power, on the premise of maintaining the stability of the battery bus, the capacitor charger 200 can charge the energy storage capacitor 400 with an appropriate power (for example, the first control value is selected). At this case, the high voltage conversion circuit 500 in the third stage of conversion can work normally, and output a high voltage and generate a specified dose of X-rays. If the battery 100 is in a low charge state, although the battery charger 300 in the first stage of conversion can provide power, on the premise of protecting the battery from excessive discharge, the capacitor charger 200 can charge the energy storage capacitor 400 with an appropriate power (for example, the second control value is selected). At this case, the high voltage conversion circuit 500 in the third stage of conversion can work normally, and output a high voltage and generate a specified dose of X-rays. If the battery 100 is in a normal state, the capacitor charger 200 can charge the energy storage capacitor 400 with a rated maximum power (for example, the third control value is selected). The high voltage conversion circuit 500 in the third stage of conversion can work normally, and output a high voltage and generate a specified dose of X-rays.

When the input end of the battery charger 300 is not connected to the power grid 101. At this time, if the battery 100 is in the normal state, the capacitor charger 200 can charge the energy storage capacitor with the rated maximum power. The high voltage conversion circuit 500 in the third stage of conversion can work normally, and output a high voltage and generate a specified dose of X-rays. At this time, the control in the normal state is substantially similar to the control when the battery charger 300 is connected to the power grid 101, no further description here. If the battery 100 is in the failure state or in a low charge state, the capacitor charger 200 does not work, the high voltage conversion circuit 500 in the third stage of conversion cannot work, a high voltage cannot be output, and the X-ray cannot be generated, that is, the X-ray machine cannot be turned on or can only be in a standby state.

In some embodiments, the battery may have only two working states according to the battery information. For example, it is determined whether the battery is in the normal state or in the failure state, that is, in some cases, the low charge state of the battery may not be considered or may not be considered alone. At this time, it is only required to select the first control value and the third control value according to whether the battery is in the failure state or whether the battery is in the normal state. In some embodiments, it is determined whether the battery is in the failure state, if the battery is in the failure state, the first control value is selected; if it is determined that the battery does not fail, the third control value is selected; the circuit parameter information of the capacitor charger is acquired and the capacitor charger is controlled based on the circuit parameter information and the first control value or the third control value. In some other embodiments, it is determined whether the battery is in the normal state, if the battery is in the normal state, the third control value is selected; if the battery is not in the normal state, the first control value is selected; the circuit parameter information of the capacitor charger is acquired and the capacitor charger is controlled based on the circuit parameter information and the first control value or the third control value. Wherein, the low charge state can also be classified into failure state or normal state. The corresponding controls all belong to the protection scope of the present disclosure.

Further, in some embodiments, if the battery is in the failure state, and if the control unit 110 acquires the output power of the capacitor charger 200, the first control value can be set as a first output power reference value; if the control unit 110 acquires the input voltage of the capacitor charger 200, the first control value can be set as a first input voltage reference value; if the control unit 110 acquires the input current of the capacitor charger 200, the first control value can be set as a first input current reference value. And then, the control unit 110 can obtain a difference value according to corresponding circuit parameter information and a corresponding reference value, and generate a state operation signal based on the difference value according to a preset control algorithm to control the capacitor charger 200.

In some embodiments, if the battery is in the low charge state, and if the control unit 110 acquires the output power of the capacitor charger 200, the second control value can be set as a second output power reference value; if the control unit 110 acquires the input voltage of the capacitor charger 200, the second control value can be set as a second input voltage reference value; if the control unit 110 acquires the input current of the capacitor charger 200, the second control value can be set as a second input current reference value. And then, the control unit 110 can obtain a difference value according to corresponding circuit parameter information and a corresponding reference value, and generate a state operation signal based on the difference value according to a preset control algorithm to control the capacitor charger 200.

In some embodiments, if the battery is in the normal state, and if the control unit 110 acquires the output power of the capacitor charger 200, the third control value can be set as a third output power reference value; if the control unit 110 acquires the input voltage of the capacitor charger 200, the third control value can be set as a third input voltage reference value; if the control unit 110 acquires the input current of the capacitor charger 200, the third control value can be set as a third input current reference value. And then, the control unit 110 can obtain a difference value according to corresponding circuit parameter information and a corresponding reference value, and generate a state operation signal based on the difference value according to a preset control algorithm to control the capacitor charger 200.

By using the adaptive control method of the above embodiment, different charging strategies of the capacitor charger 200 can be adaptively selected according to different working states of the battery 100, thereby ensuring that the high voltage generator 10 can operate in an optimal state, improving the reliability of operating, and then improving the stability of the X-ray machine.

Figure 5:
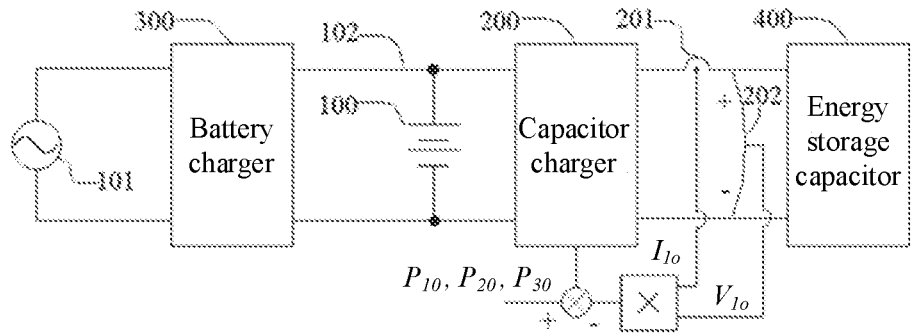
FIG. 5 is a control logic circuit diagram I of a controller according to an embodiment of the present disclosure.

Further, referring to FIG. 5, in an embodiment, the acquired circuit parameter information is the output power of the capacitor charger 200. So the first control value $C_1$ can be set as the first output power reference value $P_{10}$, the second control value $C_2$ can be set as the second output power reference value $P_{20}$, and the third control value $C_3$ can be set as the third output power reference value $P_{30}$. That is, the control unit 110 obtains a difference value between the output power of the capacitor charger 200 and a corresponding output power reference value under a corresponding operating working state. The control unit 110 generates a state operation signal based on the difference value according to a preset control algorithm, to adjust the output power of the capacitor charger 200. The control unit 110 can detect an output current and an output voltage of the capacitor charger 200 through the output current sampling unit 201 and the output voltage sampling unit 202, and multiply the output current by the output voltage to obtain the output power. In an embodiment, the output current sampling unit 201 can be a current sensor, the output voltage sampling unit 202 can be a voltage sensor or a resistance sampling circuit, or the like, and the present disclosure is not limited thereto. In an embodiment, the preset control algorithm can be a Proportion Integral Differential (PID) algorithm, and the preset control algorithm can also be other control algorithms, which can be set according to actual requirements. Further, the preset control algorithms in different state may be different, and parameters of preset control algorithms may also be different, the and the present disclosure is not limited thereto.

Specifically, for example, if the battery 100 fails, the control unit 110 can obtain a difference value between the output power and the first output power reference value $P_{10}$. At the same time, the control unit 110 can generate a state operation signal based on the difference value according to a preset control algorithm, and adjust the output power of the capacitor charger 200 according to the state operation signal. The first output power reference value $P_{10}$ can be set according to the rated output power of the battery charger 300.

Similarly, if the residual charge of the battery 100 is too low, the control unit 110 loads second output power reference value $P_{20}$ and obtains a difference value between the output power and the second output power reference value $P_{20}$. At the same time, the control unit 110 can generate a state operation signal based on the difference value according to a preset control algorithm, and adjust the output power of the capacitor charger 200 according to the state operation signal. The second output power reference value $P_{20}$ can be set according to the rated output power of the battery charger 300. Wherein, the preset control algorithm in failure state and the preset control algorithm in low charge state may be different.

The rated output power $P_{0o(max)}$ of the battery charger 300 is taken as a reference value, a smaller amount $\varepsilon_p$ can be subtracted from the rated output power $P_{0o(max)}$ to set the first output power reference value $P_{10}$ and the second output power reference value $P_{20}$. For example, it can be represented as:

$$C_1 = C_2 = P_{10} = P_{20} = P_{0o(max)} - \varepsilon_p$$

For example, if the rated output current $P_{0o(max)}$ satisfies $P_{0o(max)} = 1$ kW, the first output power reference value $P_{10}$ and the second output power reference value $P_{20}$ can be set about 900 W. In other embodiments, the second output power reference value and the third output power reference value can be set according to actual conditions, which are not limited there, and the second output power reference value may be or may not be equal to the third output power reference value.

If the residual charge of the battery 100 is normal, that is, the high voltage generator 10 is operated normally, the control unit 110 can load the third output power reference value $P_{30}$ and obtain a difference value between the output power and the third output power reference value $P_{30}$, at the same time the control unit 110 can generate a state operation signal based on the difference value according to the preset control algorithm, and adjust the output power of the capacitor charger 200 according to the state operation signal. Wherein, the preset control algorithm in failure state, the preset control algorithm in low charge state and the preset control algorithm in normal state may be different.

The third output power reference value $P_{30}$ can be set according to an upper limit value of the output power of the capacitor charger 200. The maximum power $P_{1o(max)}$ of the capacitor charger 200 is taken as a reference value, the third output power reference value can be set as the maximum power $P_{1o(max)}$ of the circuit, for example, it may be represented as:

$$C_3 = P_{30} = P_{1o(max)}$$

In some other embodiments, the third output power reference value $P_{30}$ can be set according to actual conditions, and the present disclosure is not limited thereto.

The control unit 110 sets different control values according to the different working states of the battery 100 respectively, such as the first output power reference value, the second output power reference value, and the third output power reference value, and adjusts the output power of the capacitor charger 200 accordingly, and adaptively adjusts the charging strategy of the capacitor charger 200 under different working states, thereby improving the reliability of the operating of the high voltage generator 10.

Figure 6:
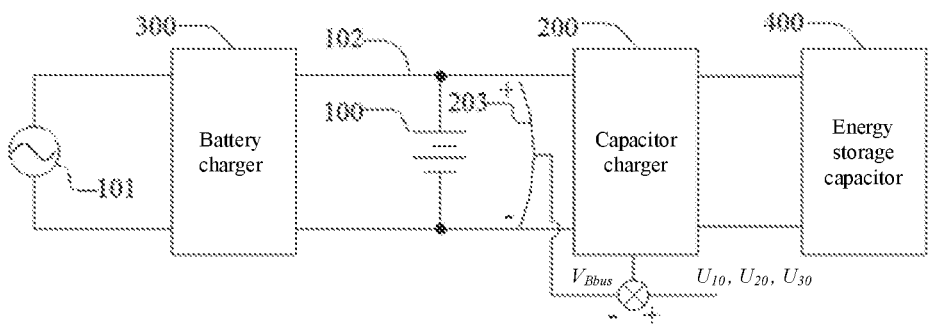
FIG. 6 is a control logic circuit diagram II of a controller according to an embodiment of the present disclosure.

Referring to FIG. 6, in an embodiment, the acquired circuit parameter information is the input voltage $V_{Bbus}$ of the capacitor charger 200. At this time, the first control value $C_1$ can be set as the first input voltage reference value $U_{10}$. The second control value $C_2$ can be set as the second input voltage reference value $U_{20}$. The third control value $C_3$ can be set as the third input voltage reference value $U_{30}$. That is, the control unit 110 obtains a difference value between the input voltage of the capacitor charger 200 and a corresponding input voltage reference value under a corresponding working state. Further, the control unit 110 obtains a state operation signal based on the difference value according to a preset control algorithm, to adjust the input voltage of the capacitor charger 200. Wherein, the control unit 110 can detect the input voltage of the capacitor charger 200 through the input voltage sampling unit 203, the input voltage of the capacitor charger 200 can be considered as the battery voltage $V_{Bbus}$. In an embodiment, the input voltage sampling unit 203 can be a voltage sensor or a resistor voltage-division circuit. By controlling the input voltage, the output power of the capacitor charger 200 is finally adjusted, to match the input power and the output power.

Specifically, if the battery 100 is in failure state, the control unit 110 can obtain a difference value between the input voltage and the first input voltage reference value $U_{10}$. Further, the control unit 110 can obtain a state operation signal based on the difference value according to a preset control algorithm, and adjust the input voltage of the capacitor charger 200 according to the state operation signal. The first input voltage reference value $U_{10}$ can be set according to the highest voltage of the battery 100. By setting the first input voltage reference value, when the battery 100 is disconnected from the battery bus 102 due to a fault, a voltage of the battery bus 102 can be maintained at a high value to ensure that the transmission power of the capacitor charger 200 is at a high level.

The highest voltage $U_{B(max)}$ of the battery 100 is taken as a reference value, the first input voltage reference value $U_{10}$ is set by subtracting a smaller amount $\varepsilon_{Umax}$ from the highest voltage $U_{B(max)}$. For example, it can be represented as:

$$C_1=U_{10}=U_{B(max)}-\varepsilon_{Umax}$$

For example, if the highest voltage $U_{B(max)}$ of the battery 100 is 52V, the first input voltage reference value can be set as 50V. The specific value of the first input voltage reference value $U_{10}$ can be set according to actual conditions, which is not limited by the present disclosure.

When the battery 100 is in a low charge state, the control unit 110 selects the second input voltage reference value $U_{20}$, and obtains a difference value between the input voltage and the second input voltage reference value $U_{20}$. The control unit 110 generate a state operation signal based on the difference value according to a preset control algorithm, and can further adjust the input voltage of capacitor charger 200 according to the state operation signal.

The second input voltage reference value $U_{20}$ can be set according to the lowest voltage of the battery 100. By setting the second input voltage reference value, the output power can be automatically adjusted and changed to ensure that the battery 100 will not be over-discharged with a large current.

If the residual charge of the battery 100 is normal, the control unit 110 loads the third input voltage reference value $U_{30}$, and can obtain a difference value between the input voltage and the third input voltage reference value $U_{30}$. In addition, the control unit 110 can generate a state operation signal based on the difference value according to a preset control algorithm, and adjust the input voltage of the capacitor charger 200 according to the state operation signal. The third input voltage reference value $U_{30}$ can be set according to the lowest voltage of the battery 100. When the high voltage generator 10 operates normally, a stable power supply to the third stage can be ensured by setting the third input voltage reference value $U_{30}$.

The lowest voltage $U_{B(min)}$ of the battery 100 is taken as a reference, the second input voltage reference value $U_{20}$ and the third input voltage reference value $U_{30}$ can be set by adding a smaller amount $\varepsilon_{Umin}$ to the lowest voltage $U_{B(min)}$. For example, it can be represented as:

$$C_2=C_3=U_{20}=U_{30}=U_{B(min)}+\varepsilon_{Umin}$$

For example, if the lowest voltage $U_{B(min)}$ of the battery 100 is 40V, the second input voltage reference value $U_{20}$ and the third input voltage reference value $U_{30}$ can be set as 42V. In some embodiments, the second input voltage reference value $U_{20}$ and the third input voltage reference value $U_{30}$ can be set according to actual conditions, which are not limited there, and the second input voltage reference value may be or may not be equal to the third input voltage reference value.

The control unit 110 controls the input voltage of the capacitor charger 200 according to the different working states of the battery 100, and then adjusts the output power of the capacitor charger 200, thereby achieving adaptations to different charging strategies of the capacitor charger 200, and improving the reliability of the operating of the high voltage generator 10.

Figure 7:
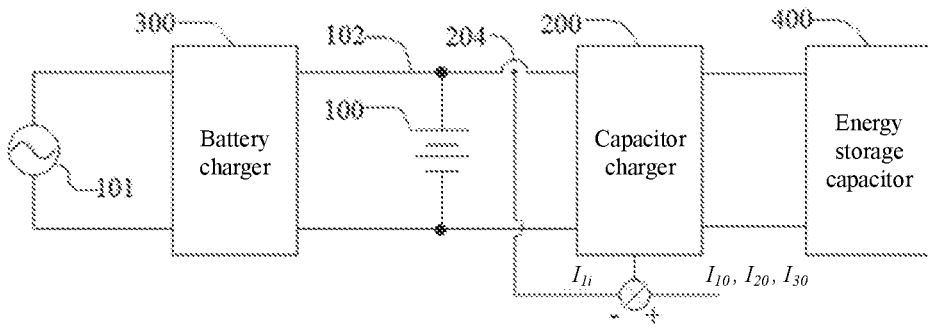
FIG. 7 is a control logic circuit diagram III of a controller according to an embodiment of the present disclosure.

Referring to FIG. 7, in an embodiment, the circuit parameter information of the capacitor charger 200 is the input current $I_{1i}$ of the capacitor charger 200. At this time, the first control value $C_1$ can be set as the first input current reference value $I_{10}$. The second control value $C_2$ can be set as the second input current reference value $I_{20}$. The third control value $C_3$ can be set as the third input current reference value $I_{30}$. Further, the control unit 110 obtains a difference value between the input current of the capacitor charger 200 and a corresponding input current reference value selected under a corresponding working state, and generates a state operation signal based on the difference value according to different preset control algorithm to adjusts the input current of the capacitor charger 200. The control unit 110 can detect the input current $I_{1i}$ of the capacitor charger 200 through the input current sampling unit 204. In an embodiment, the input current sampling unit 204 can be a current sensor or the like.

Specifically, for example, when the battery 100 is in failure state, the control unit 110 obtains a difference value between the input current and the first input current reference value $I_{10}$. Further, the control unit 110 obtains a state operation signal based on the difference value according to a preset control algorithm, and adjusts the input current of the capacitor charger 200 according to the state operation signal. The first input current reference value $I_{10}$ can be set according to the rated output current of the battery charger 300. When the battery 100 fails and the battery 100 is disconnected from the battery bus 102, through the first input current reference value $I_{10}$, it can be ensured that the voltage on the battery bus 102 is controlled by the battery charger 300.

When the battery 100 is in the low charge state, the control unit 110 can obtain a difference value between the input current and the second input current reference value $I_{20}$. The control unit 110 generates a state operation signal based on the difference value according to a preset control algorithm, and adjusts the input current of the capacitor charger 200 according to the state operation signal. The second input current reference value $I_{20}$ can be set according to the rated output current of the battery charger 300, which can be ensured that the current flowing out of the battery bus 102 is less than the maximum inflow current (that is, the input current of the battery charger 300). When the battery 100 is in the low charge state, it can be ensured that the battery 100 is in a charging state.

In some embodiments, the first input current reference value $I_{10}$ and the second input current reference value $I_{20}$ can be set according to the rated output current of the battery charger 300. The rated output current $I_{0o(max)}$ of the battery charger 300 is taken as a reference value, the first input current reference value $I_{10}$ and the second input current reference value $I_{20}$ are set by subtracting a smaller amount $\varepsilon_I$ from the rated output current $I_{0o(max)}$. For example, it can be represented as:

$$C_1 = C_2 = I_{10} = I_{20} = I_{0o(max)} - \varepsilon_I$$

For example, if the rated output current $I_{0o(max)}$ satisfies $I_{0o(max)} = 10$ A, the first input current reference value $I_{10}$ and the second input current reference value $I_{20}$ can be set about 8 A. In some embodiments, the first input current reference value $I_{10}$ and the second input current reference value $I_{20}$ can be set according to actual conditions, which are not limited there, and the first input voltage reference value $I_{10}$ may be or may not be equal to the second input voltage reference value $I_{20}$.

When the charge of the battery 100 is normal, that is, the high voltage generator 10 works normally at this time, the control unit 110 loads the third input current reference value $I_{30}$ and can obtain a difference value between the input current and the third input current reference value $I_{30}$. The control unit 110 can obtain a state operation signal based on the difference value according to a preset control algorithm, and adjust the input current of the capacitor charger 200 according to the state operation signal. The third input current reference value $I_{30}$ can be set according to the rated input current of the capacitor charger 200. For example, the third input current reference value $I_{30}$ can be set above the rated input current $I_{1i(max)}$ of the capacitor charger or not limited, for example, it may be represented as: $C3 = I_{30} \geq I_{1i(max)}$. By setting the third input current reference value $I_{30}$, the battery charger can be guaranteed to work at the maximum power.

In the embodiments of FIG. 5, FIG. 6, and FIG. 7, the first control value $C_1$, the second control value $C_2$, and the third control value $C_3$ are set to variables with same control type, but the present disclosure is not limited thereto. In some embodiments, the first control value $C_1$, the second control value $C_2$, and the third control value $C_3$ can be set to variables with different control type. For example, the first control value $C_1$ can be set as a first output power reference value $P_{10}$, the second control value $C_2$ can be set as a second input voltage reference value $U_{20}$, and the third control value $C_3$ can be set as a third input current reference value $I_{30}$.

Wherein, the preset control algorithm in failure state, the preset control algorithm in low charge state and the preset control algorithm in normal state may be different. And, the preset control algorithms may also be different according to the different circuit parameter information.

The control unit 110 can control the input current of the capacitor charger 200 according to the different working states of the battery 100, accordingly adjust the output power of the capacitor charger 200, thereby implementing the charging strategies of the capacitor charger 200 in different states and improving the reliability of the operating of the high voltage generator 10.

Figure 8:
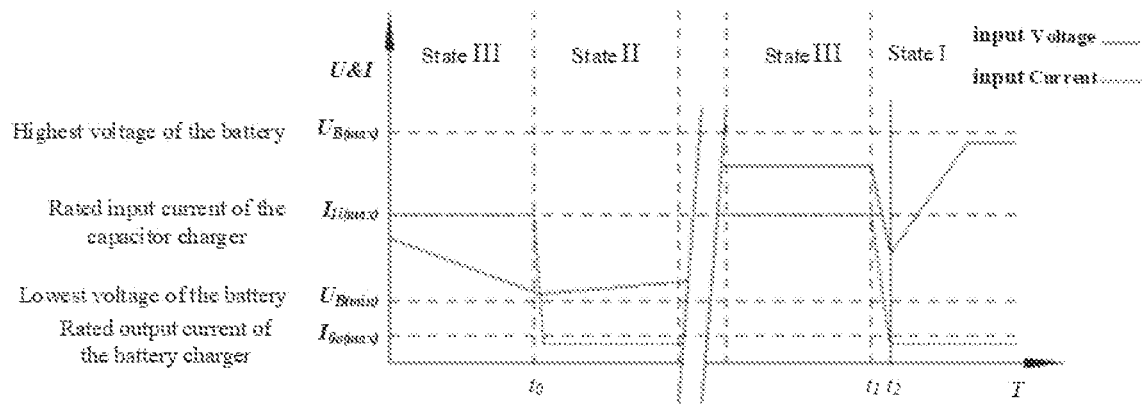
FIG. 8 shows waveforms of input current and input voltage of the capacitor charger in different states according to an embodiment of the present disclosure.

FIG. 8 shows waveforms of input current and input voltage of the capacitor charger 200. For example, the battery is in a state III (normal state) until a moment $t_0$. At the moment $t_0$, the control unit 110 detects that the charge of the battery 100 is too low or the battery 100 is undervoltage, and switches from the state III to a state II (low charge state) at this time. The second control value of above three types of control logic (such as the output power, the input voltage and the input current) is selected, to reduce the input current of the capacitor charger 200, and reduce the input current of the capacitor charger 200 below the rated output current $I_{0o(max)}$ of the battery charger 300. When the input current is stable, less energy flows into the battery 100. The voltage of battery 100 can be slowly recovered, and the state of the battery 100 can be changed from the state II (low charge state) to the state III (normal state).

For example, at a moment $t_1$, the control unit 110 determines that the battery 100 is failed, and the battery 100 is switched from the state III (normal state) to the state I (failure state). Due to the lack of the battery 100 for supporting the voltage of battery bus 102, the first control value is selected of the above three types of control logic (such as the output power, the input voltage, and the input current), which can reduce the input voltage and the output power of the capacitor charger 200, and can make the input current of the capacitor charger 200 stable and less than the rated output current $I_{0o(max)}$ of the battery charger 300 after the moment $t_2$. After that, the voltage is recovered and finally is stabilized near a low voltage reference value (according to input voltage control) or the highest voltage of the battery 100 (input current control or output power control).

In an embodiment, the control unit 110 can acquire fault information and charge information, and the like of the battery 100 through a battery management system. In some other embodiments, the control unit 110 can detect an input voltage $U_B$ of the capacitor charger 200 in a current sampling period and an input voltage $U_B'$ of the capacitor charger 200 in a previous sampling period, through a voltage sampling unit (such as a voltage sensor, a resistance sampling circuit, and the like). A voltage difference between two sampled input voltages in two adjacent sampling periods is obtained and an absolute value of the voltage difference is $|\Delta U_B|$. The absolute value $|\Delta U_B|$ is compared to a preset change reference value $\Delta U_{Bref}$. If $|\Delta U_B| > \Delta U_{Bref}$, it is indicated that the voltage of the battery bus 102 varies too much, and the battery may be disconnected from the battery bus 102, and the battery 100 is in the failure state. When it is determined that the battery 100 is in the failure state, then the first control value $C_1$ is selected. If the absolute value $|\Delta U_B|$ is less than or equal to a preset change reference value $\Delta U_{Bref}$, it is indicated that the battery 100 does not fail. Wherein, the input voltage of the capacitor charger 200 is the voltage of the battery 100.

Further, if $|\Delta U_B| \leq \Delta U_{Bref}$, it is determined that the battery 100 does not fail, then the input voltage $U_B$ sampled in the current sampling period is compared to a preset voltage reference value $U_{up}$. If the input voltage $U_B$ sampled in the current sampling period is less than the preset voltage reference value $U_{up}$, that is, $U_B<U_{up}$, it is determined that the charge of the battery 100 is too low, the battery 100 is in low charge state and the second control value $C_2$ is selected at this time. If the input voltage sampled in the current sampling period is greater than or equal to the preset voltage reference value, that is, $U_B \geq U_{up}$, it is determined that the charge of the battery 100 is normal, and the third control value $C_3$ is selected at this time. In an embodiment, the preset voltage reference value $U_{up}$ may be 10% of the rated voltage of the battery 100. In an embodiment, the sampling period can be set according to actual requirements, for example, 100 μs.

In an embodiment, the output current and output voltage of the capacitor charger 200 can also be acquired through the output current sampling unit 201 and the output voltage sampling unit 202. In an embodiment, the output current sampling unit 201 can be a current sensor. The output voltage sampling unit 202 can be a voltage sensor or a resistance sampling circuit.

Figure 9:
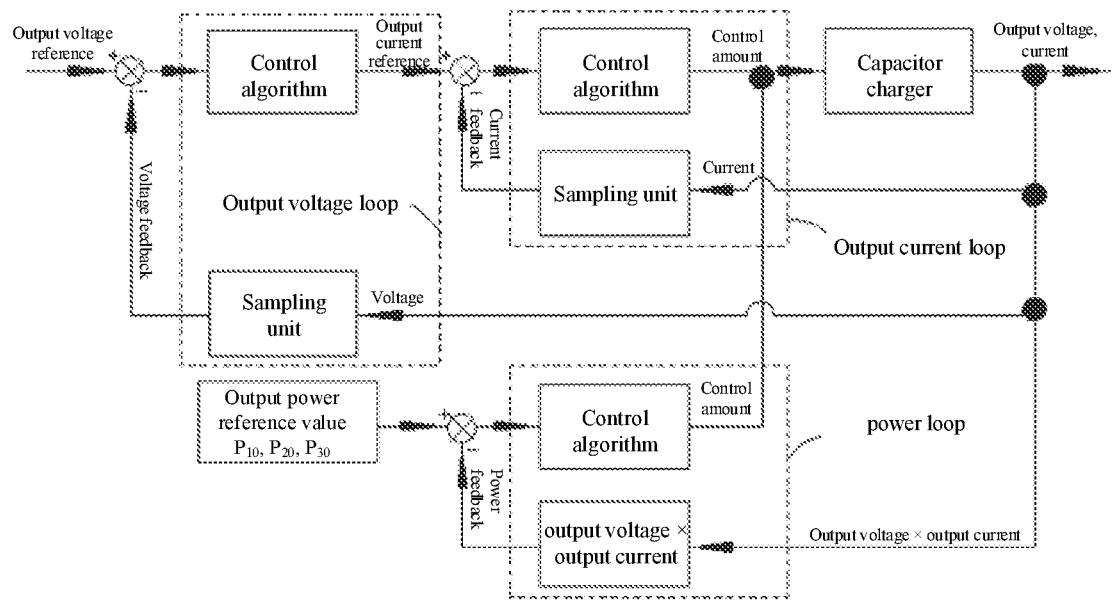
FIG. 9 is a control logic block diagram according to an embodiment of the present disclosure.

Further, FIG. 9 is a control logic block diagram of a capacitor charger according to an embodiment. As shown in FIG. 9, in an embodiment, the control unit 110 compares the output voltage of the capacitor charger 200 to the output voltage reference and generates an output voltage operation signal. The control unit 110 takes the output voltage operation signal as an output current reference and compares the output current reference to the output current of the capacitor charger 200, and generates an output current operation signal; and at the same time, a competitive output between the output current operation signal and the state operation signal (an output of an output power loop) is performed. In the FIG. 9, the output power is taken as an illustration, that is, different output power reference values are loaded according to the state of the battery to perform the control. In other embodiments, input voltage or input current can also be selected for control.

Figure 10:
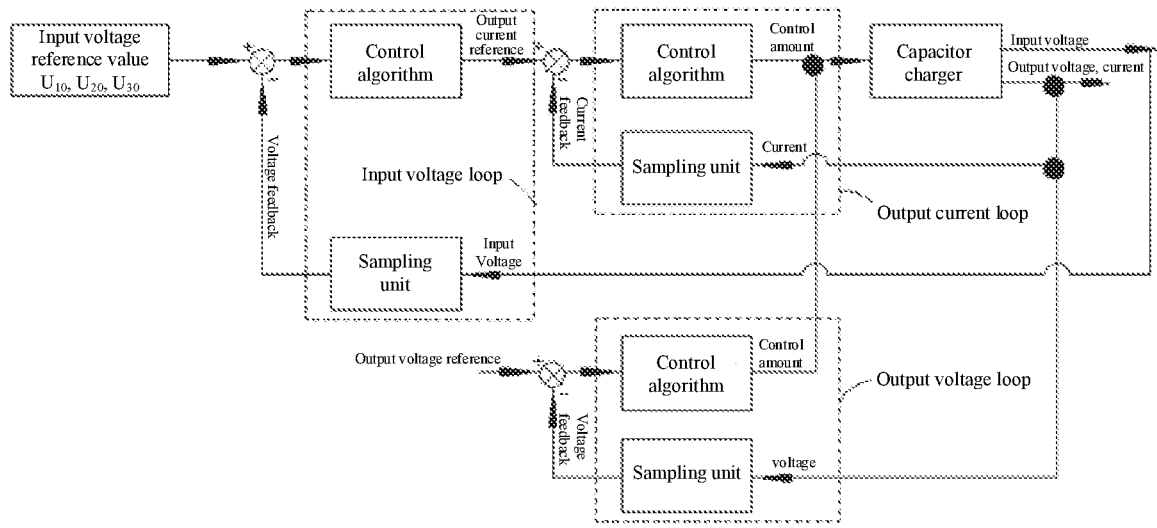
FIG. 10 is a control logic block diagram according to another embodiment of the present disclosure.

FIG. 10 is a control logic block diagram of a capacitor charger according to another embodiment. As shown in FIG. 10, the control unit 110 can take the state operation signal (an output of an input voltage loop) as an output current reference and compares the output current reference to the output current of the capacitor charger 200, and generates an output current operation signal. At the same time, the control unit 110 can compare the output voltage of the capacitor charger 200 to the output voltage reference, and generates an output voltage operation signal. Then competitive output between the output voltage operation signal and the output current operation signal is performed, that is, a stronger signal between the output voltage operation signal and the output current operation signal is output. In the FIG. 10, the input voltage is taken as an illustration, that is, different input voltage reference values are loaded according to the state of the battery to perform control. In other embodiments, input power or input current can also be selected for control.

In the present disclosure, by using the steps of the adaptive control method of the above embodiment, the capacitor charger 200 can be adaptively controlled to use different charging strategies according to different working states of the battery 100, thereby ensuring that the high voltage generator 10 can operate in an optimal state, improving the reliability of operating, and then improving the stability of the X-ray machine.

Further, in some embodiments, the control unit 110 includes a system controller and a capacitor charging controller. The system controller is electrically connected to the battery 100. The system controller acquires the operating information of the battery 100 through a battery management system. The operating information of the battery includes: fault information, battery voltage, battery current and State of Charge (SOC) information and the like. And the system controller determines that the battery is in a failure state, a low charge state or a normal state according to the operating information of the battery 100. The capacitor charging controller is electrically connected to the capacitor charger 200, and communicates and exchanges information with the system controller. The capacitor charging controller is configured to sample the circuit parameter information of the capacitor charger 200, and perform a corresponding operation according to the state of the battery to further control the capacitor charger. For example, the capacitor charging controller is configured to sample the input voltage, or the input current, or the like of the capacitor charger 200.

Further, the system controller is in communication with the capacitor charging controller, which exchange information with each other, and work in coordination with each other. The system controller communicates directly with the battery management system, to comprehensively acquire the battery information and obtain all information needed for the determination, such as the battery voltage, the current, the SOC, and the failure state. However, a communication interval is generally long and the communication has a longer delay, which makes the information update slow. In practice, a battery fault may occur before the battery communicates with the system controller. The voltage on the battery bus 102 can drop due to power imbalance, bringing the system down, or triggering a relatively serious protection, which seriously affects the system stability and the usage experience. Therefore, the state of the battery can be complementally determined by the capacitor charging controller. Since the residual charge of the battery is positively related to the voltage of the battery bus 102, the capacitor charging controller can detect the voltage of the battery 100. The state of the battery 100 can be further determined according to whether the change rate of the voltage of the battery bus is too large; or the state of the battery 100 can be determined whether the battery SOC is too low. Wherein, the accuracy of battery state judgment by simply sampling the voltage is poor and the voltage of the battery bus is easily affected by the real-time current, which can easily lead to misjudgment. Therefore, the capacitor charging controller and the system controller need to develop a suitable cooperative working mechanism to maximize their advantages and avoid their disadvantages.

Figure 11:
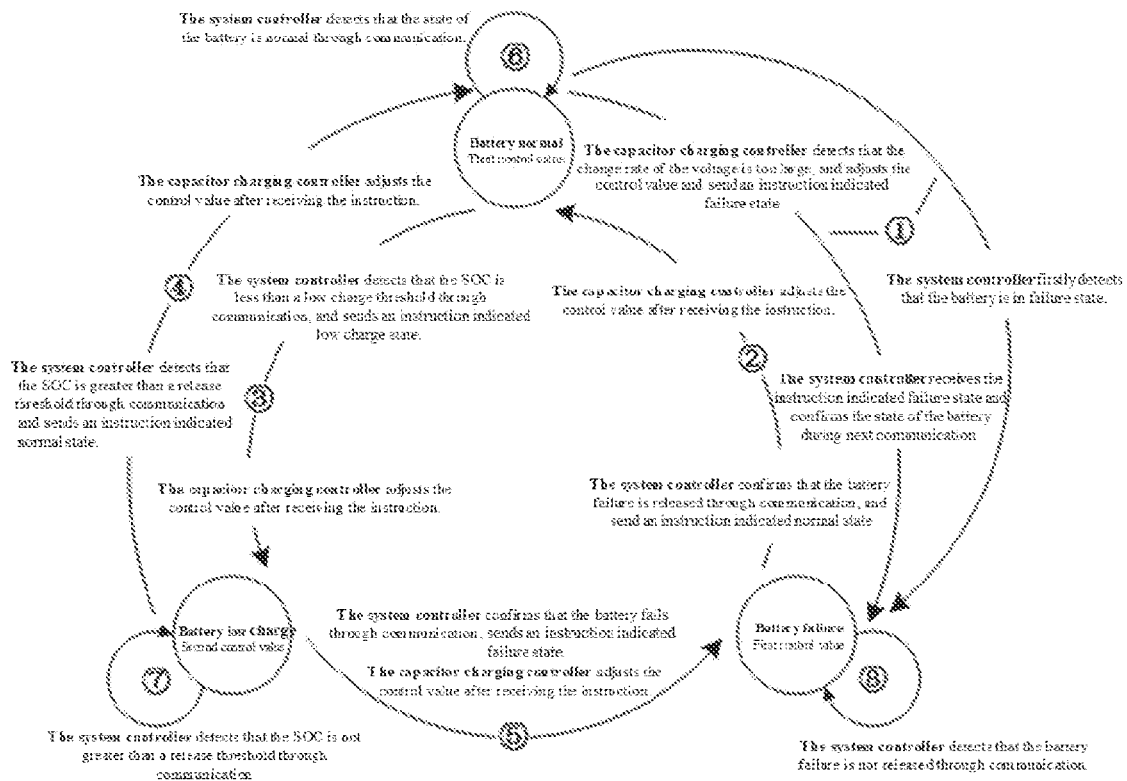
FIG. 11 is a schematic diagram of state switching of a high voltage generator provided by an embodiment of the present disclosure.

The control unit 110 including a system controller and a capacitor charging controller is taken as an example, the state diagram showing the switching between the above three states is shown in FIG. 11. The switching processes between the states can be shown in the following situations.

① Battery normal state→battery failure state: when the system controller firstly detects that the battery is in a failure state, the system controller directly loads the program corresponding to the battery failure state. At the same time, the system controller sends an instruction indicated failure state to the capacitor charging controller to inform the capacitor charging controller that the battery is in the failure state, and the capacitor charging controller will load the first control value.

In some embodiments, before the capacitor charging controller receives the instruction indicated failure state, the capacitor charging controller detects the change rate of the voltage of the battery bus 102. If the change rate is too large, the battery is considered in the failure state, and the capacitor charging controller adjusts the control value from the third control value to the first control value. Meanwhile, the capacitor charging controller reports an instruction indicated failure state (this signal can be fed back with merely 0/1 without complicated communication protocol) to the system controller. After receiving the signal indicated failure state, the system controller confirms the state of the battery once again during the next communication with the battery. If the battery does enter the failure state, the system controller will change the program to the battery failure state. Otherwise, the system controller maintains the program in the battery normal state; and at the same time, the system controller sends an instruction to the capacitor charging controller to instruct the capacitor charging controller to reload the third control value.

② Battery failure state→battery normal state: the system controller periodically communicates with the battery. When the system controller detects that the battery is in the normal state, the system controller loads the program corresponding to the battery normal state. At the same time, the system controller sends an instruction indicated normal state (this instruction can be sent with 0/1 signal without complicated communication protocol) to the capacitor charging controller. After receiving the instruction, the capacitor charging controller loads the program corresponding to the normal state, and adjusts the control value from the first control value to the third control value.

③ Battery normal state→battery low charge state: the system controller periodically communicates with the battery. When the system controller detects that the battery SOC is less than a low charge threshold through communication, the system controller loads the program corresponding to the battery low charge state. At the same time, the system controller sends an instruction indicated low charge state (this instruction can be sent with 0/1 signal without complicated communication protocol) to the capacitor charging controller. After receiving the instruction, the capacitor charging controller loads the program corresponding to a low charge state, and adjusts the control value from the third control value to the second control value.

④ Battery low charge state→battery normal state: the system controller periodically communicates with the battery. When the system controller detects that the battery SOC is greater than a release threshold (slightly greater than the low charge threshold) through communication, the system controller loads the program corresponding to the battery normal state. At the same time, the system controller sends an instruction indicated normal state (this instruction can be sent with 0/1 signal without complicated communication protocol) to the capacitor charging controller. After receiving the instruction, the capacitor charging controller loads the program corresponding to the normal state, and adjusts the control value from the second control value to the third control value.

⑤ Battery low charge state→battery failure state: the system controller periodically communicates with the battery. When the system controller confirms that the battery fails through communication, the system controller loads the program corresponding to the battery failure state. At the same time, the system controller sends an instruction indicated failure state (this instruction can be sent with 0/1 signal without complicated communication protocol) to the capacitor charging controller. After receiving the instruction, the capacitor charging controller loads the program corresponding to the failure state, and adjusts the control value from the second control value to the first control value.

⑥ Battery normal state→battery normal state: when the state of the battery acquired by the system controller through communication is the normal state, the battery normal state is maintained.

⑦ Battery failure state→battery failure state: when the state of the battery acquired by the system controller through communication is the failure state (including failure to communicate with the battery), the battery failure state is maintained.

⑧ Battery low charge state→battery low charge state: when the SOC acquired by the system controller through communication is not greater than the preset low charge release threshold, the battery low charge state is maintained.

Finally, for the condition of battery failure state→battery low charge state, in practical, it is impossible to directly switch from the battery failure state to the battery low charge state. This switching process is implemented indirectly through ②+③: for example, in one communication, the system controller acquires information indicating the battery normal state and the low charge state. During the switching of the state, the battery is firstly switched to the normal state and then to the low charge state, and finally, based on the low charge state, the system controller sends an instruction to the capacitor charger 200 to adjust the control value of the capacitor charger 200 from the first control value to the second control value.

In some embodiments, the state of the battery may be classified into only two working states based on the battery information, for example, it is determined whether the battery is in a normal state or whether the battery is in a failure state. That is, in some cases, the low charge state of the battery may not be considered or may not be considered alone. At this time, it is only needed to select the first control value and the third control value according to whether the battery is in the failure state or whether the battery is in the normal state. Therefore, it may only be necessary to perform the determinations ① and ②, but the present disclosure is not limited thereto.

In some embodiments, the capacitor charging controller can acquire the state of the battery through communication with the system controller, and select a corresponding control value, and perform an operation according to the circuit parameter information and the corresponding control value to control the capacitor charger. In some other embodiments, the system controller can select the corresponding control value according to the state of the battery, and sends the corresponding control value to the capacitor charging controller through the communication; the capacitor charging controller performs the operation according to the received control value and the circuit parameter information to obtain a state operation signal to control the capacitor charger.

From the above, regardless of whether the high voltage generator is connected to the grid or not, by using the adaptive control method of the present disclosure, the capacitor charger 200 can be adaptively controlled to use different charging strategies according to different working states of the battery 100, thereby ensuring that the high voltage generator 10 can operate in an optimal state, improving the reliability of operating, and then improving the stability of the X-ray machine.

The technical features of the above embodiments can be arbitrarily combined. To simplify the description, not all possible combinations of the technical features in the above embodiments are described. However, all of the combinations of these technical features should be considered as within the scope of the present disclosure, as long as there is no contradiction among such combinations.

The above embodiments are merely several exemplary embodiments of the present disclosure, and the description thereof is more specific and detailed, but it should not be construed as limiting the scope of the present disclosure. It should be noted that, several modifications and improvements can be made by those of ordinary skill in the art without departing from the concept of the present disclosure, and these are all within the protection scope of the present disclosure. Therefore, the protection scope of the present disclosure shall be subject to the appended claims.

What is claimed is:

1. An adaptive control method for a mobile X-ray machine, comprising:
   acquiring operating information of a battery, and determining a state of the battery;
   selecting a first control value if it is determined that the battery is in a failure state;
   if it is determined that the battery is not in the failure state, determining whether a residual charge of the battery is less than a low charge threshold; if the residual charge of the battery is less than the low charge threshold, determining that the battery is in a low charge state, and selecting a second control value; if the residual charge of the battery is not less than the low charge threshold, determining that the battery is in a normal state, and selecting a third control value; and
   acquiring circuit parameter information of a capacitor charger, controlling the capacitor charger based on the circuit parameter information and the first control value when the battery in the failure state, and controlling the capacitor charger based on the circuit parameter information and the second control value or the third control value when the battery is not in the failure state;
   wherein the circuit parameter information comprises an input power, an output power, an input voltage, an input current and an output current of the capacitor charger,
   wherein, if the battery is in the failure state, setting the first control value as a first output power reference value or a first input voltage reference value or a first input current reference value, and obtaining a difference value according to the circuit parameter information and a corresponding reference value, and obtaining a state operation signal based on the difference value according to a preset control algorithm to control the capacitor charger.

2. The adaptive control method for the mobile X-ray machine of claim 1, wherein, the first output power reference value is set according to a rated output power of a battery charger, the first input voltage reference value is set according to a highest voltage of the battery, and the first input current reference value is set according to a rated output current of the battery charger.

3. The adaptive control method for the mobile X-ray machine of claim 1, further comprising: if the battery is in the low charge state, setting the second control value as a second output power reference value or a second input voltage reference value or a second input current reference value, obtaining a difference value according to the circuit parameter information and a corresponding reference value, and obtaining a state operation signal based on the difference value according to a preset control algorithm to control the capacitor charger.

4. The adaptive control method for the mobile X-ray machine of claim 3, wherein, the second output power reference value is set according to a rated output power of a battery charger, the second input voltage reference value is set according to a lowest voltage of the battery, and the second input current reference value is set according to a rated output current of the battery charger.

5. The adaptive control method for the mobile X-ray machine of claim 1, further comprising: if the battery is in the normal state, setting the third control value as a third output power reference value or a third input voltage reference value or a third input current reference value, obtaining a difference value according to the circuit parameter information and a corresponding reference value, and obtaining a state operation signal based on the difference value according to a preset control algorithm to control the capacitor charger.

6. The adaptive control method for the mobile X-ray machine of claim 5, wherein, the third output power reference value is set according to an upper limit value of the output power of the capacitor charger, the third input voltage reference value is set according to a lowest voltage of the battery, and the third input current reference value is set according to a rated input current of the capacitor charger.

7. The adaptive control method for the mobile X-ray machine of claim 1, wherein the operating information of the battery is acquired through a battery management system, and the operating information of the battery comprises fault information, a battery voltage, a battery current, and State of Charge (SOC) information.

8. The adaptive control method for the mobile X-ray machine of claim 1, wherein the acquiring the operating information of the battery and determining the state of the battery comprises:
   sampling an input voltage of the capacitor charger in a current sampling period and an input voltage of the capacitor charger in a previous sampling period;
   obtaining a voltage difference between two sampled input voltages in two adjacent sampling periods;
   if an absolute value of the voltage difference is greater than a preset change reference value, determining that the battery is in the failure state, and selecting the first control value;
   if the absolute value of the voltage difference is less than or equal to the preset change reference value, determining that the battery is not in the failure state, and comparing the input voltage sampled in the current sampling period to a preset voltage reference value, if the input voltage sampled in the current sampling period is less than the preset voltage reference value, determining that the battery is in the low charge state, and selecting the second control value; and
   if the input voltage sampled in the current sampling period is greater than or equal to the preset voltage reference value, determining that the battery is in the normal state, and selecting the third control value.

9. The adaptive control method for the mobile X-ray machine of claim 1, further comprising:
   sampling an output voltage and the output current of the capacitor charger;
   comparing the output voltage of the capacitor charger to an output voltage reference and generating an output voltage operation signal; and
   taking the output voltage operation signal as an output current reference and comparing the output current reference to the output current of the capacitor charger, generating an output current operation signal, and performing a competitive output between the output current operation signal and the state operation signal.

10. The adaptive control method for the mobile X-ray machine of claim 1, further comprising:
sampling an output voltage and the output current of the capacitor charger;
taking the state operation signal as an output current reference and comparing the output current reference to the output current of the capacitor charger, generating an output current operation signal; and
comparing the output voltage of the capacitor charger to an output voltage reference, generating an output voltage operation signal, and performing a competitive output between the output voltage operation signal and the output current operation signal.

11. An adaptive control method for a mobile X-ray machine, comprising:
acquiring operating information of a battery, and determining whether the battery is in a failure state; if the battery is in the failure state, selecting a first control value; if the battery is not in the failure state, selecting a third control value; and
acquiring circuit parameter information of a capacitor charger, controlling the capacitor charger based on the circuit parameter information and the first control value when the battery in the failure state, and controlling the capacitor charger based on the circuit parameter information and the third control value when the battery is not in the failure state;
wherein the circuit parameter information comprises an input power, an output power, an input voltage, an input current and an output current of the capacitor charger,
wherein, if the battery is in the failure state, setting the first control value as a first output power reference value or a first input voltage reference value or a first input current reference value, and obtaining a difference value according to the circuit parameter information and a corresponding reference value, and obtaining a state operation signal based on the difference value according to a preset control algorithm to control the capacitor charger.

12. A high voltage generator, comprising:
a battery charger, an input end of the battery charger being configured to electrically connect to a grid;
a battery, connected to an output end of the battery charger electrically;
a capacitor charger, an input end of the capacitor charger being electrically connected to the battery;
an energy storage capacitor, connected to an output end of the capacitor charger electrically;
a high voltage conversion circuit, electrically connected between the energy storage capacitor and an X-ray generator; and
a controller, electrically connected to the battery and the capacitor charger, and configured to acquire operating information of a battery, and determine a state of the battery; wherein, the controller selects a first control value if the battery is in a failure state; and if the battery is not in the failure state, the controller determines whether a residual charge of the battery is less than a low charge threshold; if the residual charge of the battery is less than the low charge threshold, the controller determines that the battery is in a low charge state, and selects a second control value; if the residual charge of the battery is not less than the low charge threshold, the controller determines that the battery is in a normal state, and selects a third control value; and
the controller acquires circuit parameter information of a capacitor charger, and controls the capacitor charger based on the circuit parameter information and the first control value when the battery is in a failure state, and controls the capacitor charger based on the circuit parameter information and the second control value or the third control value when the battery is not in the failure state;
wherein the controller comprises a system controller and a capacitor charging controller, the system controller is electrically connected to the battery, the capacitor charging controller is electrically connected to the capacitor charger, and the system controller is in communication with the capacitor charging controller;
the system controller acquires operating information of the battery through a battery management system, and determines that the battery is in a failure state or a low charge state or a normal state according to the operating information of the battery;
wherein, the operating information includes: fault information, a battery voltage, a battery current, and State of Charge (SOC) information;
wherein the system controller selects a corresponding control value according to the state of the battery, and sends the corresponding control value to the capacitor charging controller, the capacitor charging controller obtains a difference value according to the circuit parameter information and the corresponding control value, and generates a state operation signal according to a preset control algorithm to control the capacitor charger.

13. The high voltage generator of claim 12, wherein the capacitor charging controller communicates with the system controller to acquire the state of the battery, selects a corresponding control value, and obtains a difference value according to circuit parameter information and the corresponding control value, and generates the state operation signal according to the preset control algorithm to control the capacitor charger.

14. The high voltage generator according to claim 13, wherein the capacitor charging controller samples an input voltage of the capacitor charger, and when detecting that a change rate of the input voltage is greater than a preset change reference value, the capacitor charging controller selects a first control value for operation, and reports fault information to the system controller.

15. The high voltage generator of claim 14, wherein the system controller determines the state of the battery once again according to the fault information sent by the capacitor charging controller and the operating information of the battery, and sends state of the battery or a corresponding control value to the capacitor charging controller.

* * * * *